US00PP36471P2

(12) United States Plant Patent
Dale Hartman

(10) Patent No.: US PP36,471 P2
(45) Date of Patent: Feb. 18, 2025

(54) ***CALADIUM* PLANT NAMED 'FRH OF13-246'**

(50) Latin Name: ***Caladium* X *hortulanum***
Varietal Denomination: FRH OF13-246

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,757

(22) Filed: May 7, 2024

(51) Int. Cl.
*A01H 5/12* (2018.01)
*A01H 6/10* (2018.01)

(52) U.S. Cl.
USPC ..... Plt./373

(58) Field of Classification Search
None
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'FRH OF13-246', characterized by its upright plant habit and tall in height; dense, leafy and bushy appearance; moderately vigorous growth habit and rapid growth rate; fancy-type leaves that have deep red-colored centers surrounded by dark green flushed with dark red-colored marginal areas and dark red-colored venation; and petioles that are close to black in color.

4 Drawing Sheets

Figure 1:
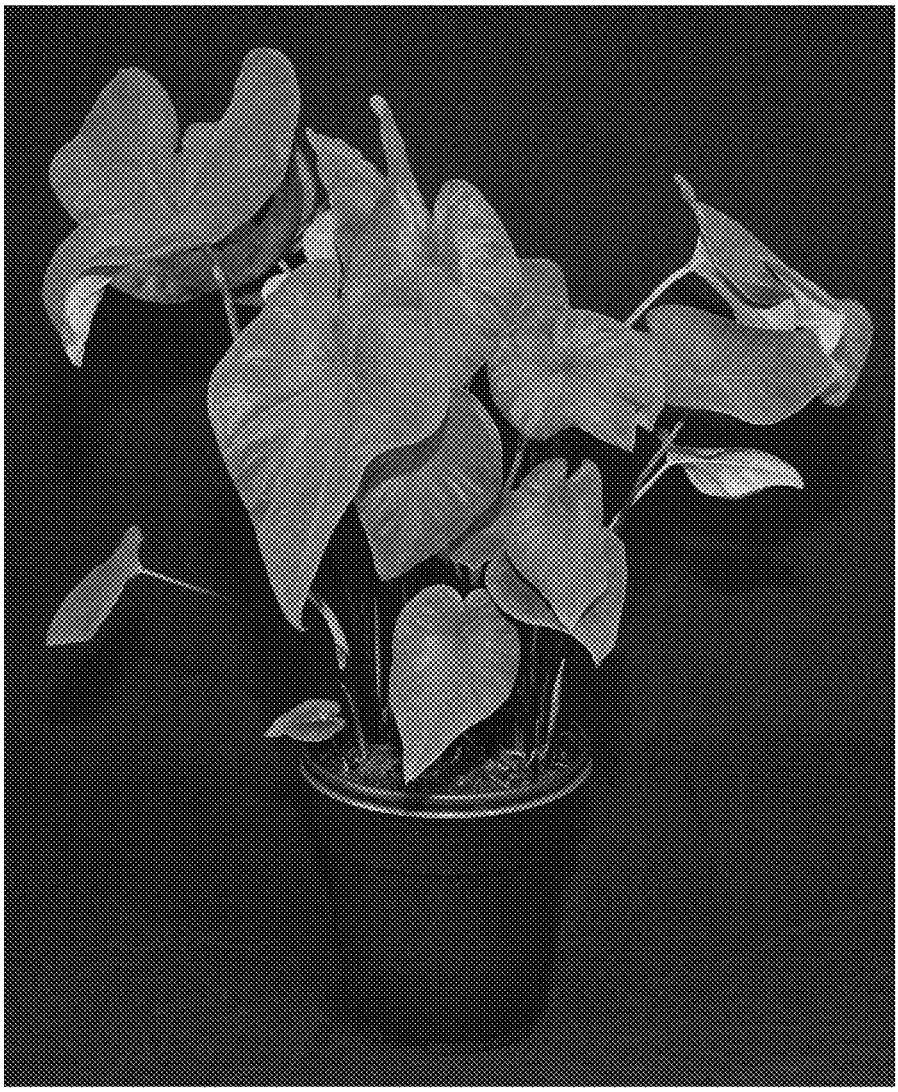

Botanical designation: *Caladium* X *hortulanum.*
Cultivar denomination: 'FRH OF13-246'.

BACKGROUND OF THE INVENTION

The present invention relates to a new and distinct cultivar of *Caladium* plant, botanically known as *Caladium* X *hortulanum,* commercially referred to as a fancy leaf-type *Caladium* and hereinafter referred to by the name 'FRH OF13-246'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2012 in Avon Park, Florida of *Caladium* X *hortulanum* 'RUF 1522-3', disclosed in U.S. Plant Pat. No. 33,615, as the female, or seed, parent with *Caladium* X *hortulanum* 'Frieda Hemple', not patented, as the male, or pollen, parent. The new *Caladium* plant was discovered and selected by the Inventor as a single plant within the progeny of the stated cross-pollination in a controlled outdoor nursery environment in Avon Park, Florida in September 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FRH OF13-246'. These characteristics in combination distinguish 'FRH OF13-246' as a new and distinct *Caladium* plant:

1. Upright plant habit and tall in height; dense, leafy and bushy appearance.
2. Moderately vigorous growth habit and rapid growth rate.
3. Fancy-type leaves that have deep red-colored centers surrounded by dark green flushed with dark red-colored marginal areas and dark red-colored venation.
4. Petioles that are close to black in color.

Plants of the new *Caladium* differ primarily from plants of the female parent, 'RUF 1522-3', in the following characteristics:

1 Plants of the new *Caladium* are taller and more upright than plants of plants of 'RUF 1522-3'.
2. Leaves of plants of the new *Caladium* are not as thick as leaves of plants of 'RUF 1522-3'.
3. Leaves of plants of the new *Caladium* have deep red-colored centers surrounded by dark green flushed with dark red-colored marginal areas and dark red-colored venation whereas leaves of plants of 'RUF 1522-3' are dark red in color with dark green-colored margins.
4. Petioles of plants of the new *Caladium* are close to black in color whereas petioles of plants of 'RUF 1522-3' are tannish pink in color with greenish brown-colored stripes, streaks, stippling and tessellations.

Plants of the new *Caladium* differ primarily from plants of the male parent, 'Frieda Hemple', in the following characteristics:

1. Plants of the new *Caladium* are taller than plants of 'Frieda Hemple'.

2. Leaves of plants of the new *Caladium* have deep red-colored centers surrounded by dark green flushed with dark red-colored marginal areas and dark red-colored venation whereas leaves of plants of 'Frieda Hemple' are medium green in color with bright red-colored centers and venation.
3. Petioles of plants of the new *Caladium* are close to black in color whereas petioles of plants of 'Frieda Hemple' are tannish pink in color with dense brownish black-colored stippling and streaks.

Plants of the new *Caladium* can be compared to plants of *Caladium* X *hortulanum* 'Postman Joyner', not patented. In side-by-side comparisons, plants of the new *Caladium* differ primarily from plants of 'Postman Joyner' in leaf color as leaves of plants of the new *Caladium* have deep red-colored centers surrounded by dark green flushed with dark red-colored marginal areas and dark red-colored venation whereas leaves of plants of 'Postman Joyner' are dark green in color with bright red-colored centers.

Plants of the new *Caladium* can also be compared to plants of *Caladium* X *hortulanum* 'Red Flash', not patented. In side-by-side comparisons, plants of the new *Caladium* differ primarily from plants of 'Red Flash' in the following characteristics:

1. Plants of the new *Caladium* are more vigorous and grow more rapidly than plants of 'Red Flash'.
2. Plants of the new *Caladium* are not as dense as plants of 'Red Flash'.
3. Leaves of plants of the new *Caladium* have deep red-colored centers surrounded by dark green flushed with dark red-colored marginal areas and dark red-colored venation whereas leaves of plants of 'Red Flash' have red-colored venation and interveinal areas with pink and white-colored spots and dark green-colored borders.
4. Petioles of plants of the new *Caladium* are close to black in color whereas petioles of plants of 'Red Flash' are reddish pink to tannish pink in color with darker-colored stippling and stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet FIG. 1 is a side perspective view of a typical plant of 'FRH OF13-246' grown in a container that has had its tuber de-eyed prior to planting.

Figure 2:
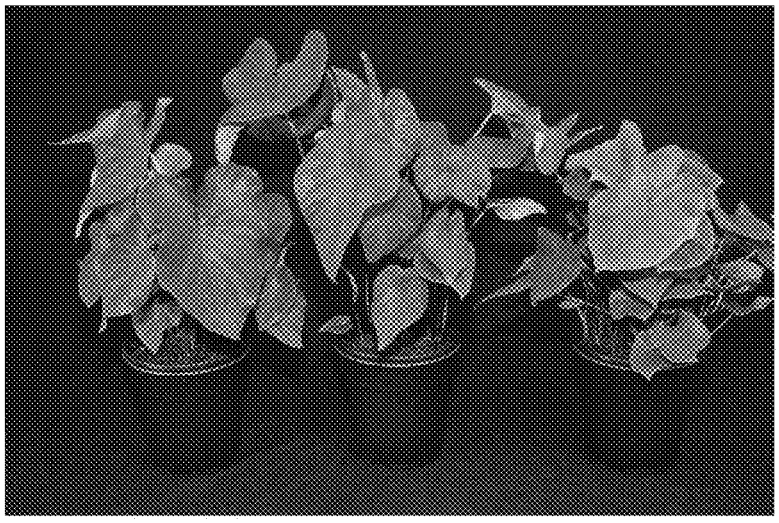

The photograph at the top of the second sheet FIG. 2 is side perspective view of typical plants of the female parent, 'RUF 1522-3' (left), 'FRH OF13-246' (center) and the male parent, 'Frieda Hemple' (right).

Figure 3:
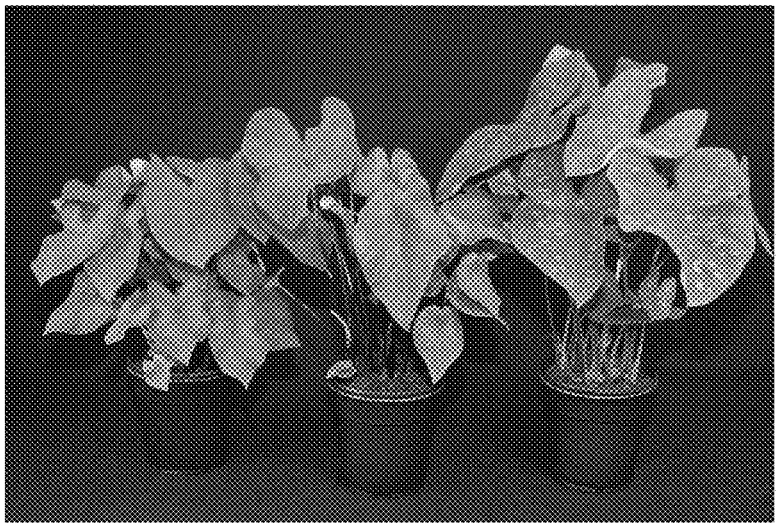

The photograph at the bottom of the second sheet FIG. 3 is side perspective view of typical plants of 'Postman Joyner' (left), 'FRH OF13-246' (center) and 'Red Flash' (right).

Figure 4:
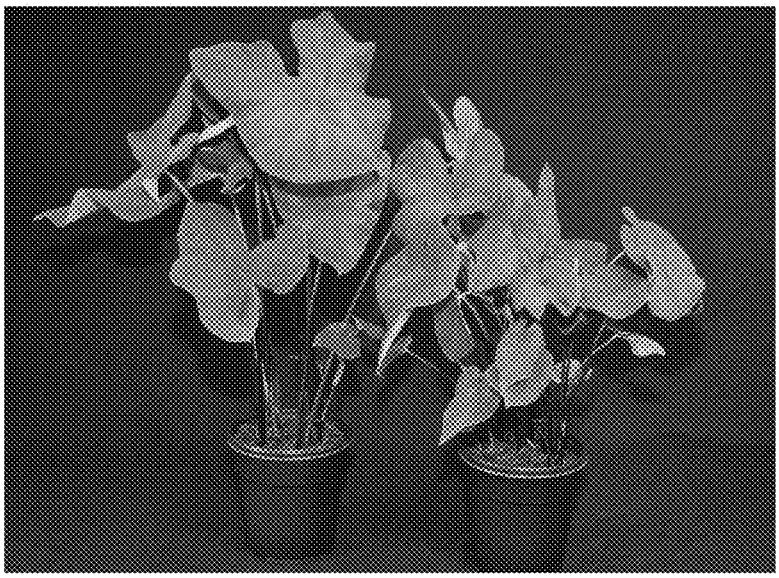

The photograph at the top of the third sheet FIG. 4 is a comparison view of typical plants of 'FRH OF13-246' grown in containers, the plant on the left has not had its tuber de-eyed and the plant on the right has had its tuber de-eyed prior to planting.

Figure 5:
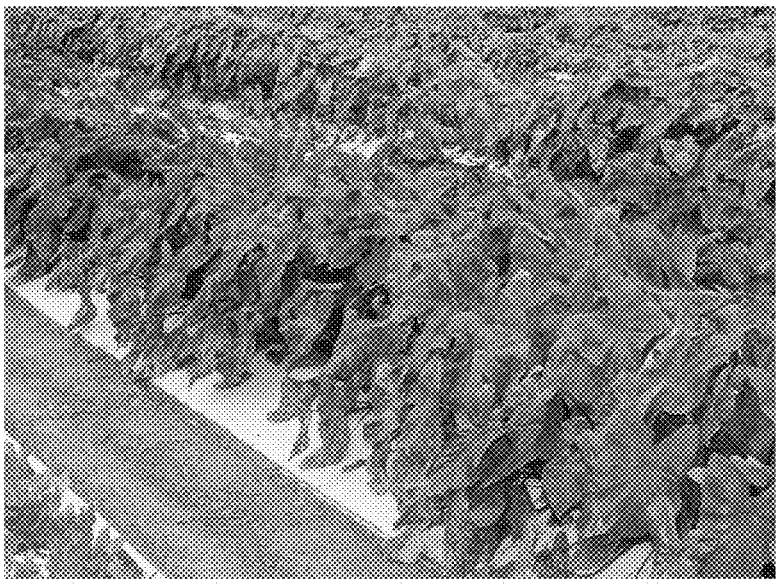

The photograph at the bottom of the third sheet FIG. 5 is a side perspective view of typical plants of 'FRH OF13-246' grown in an open production field.

Figure 6:
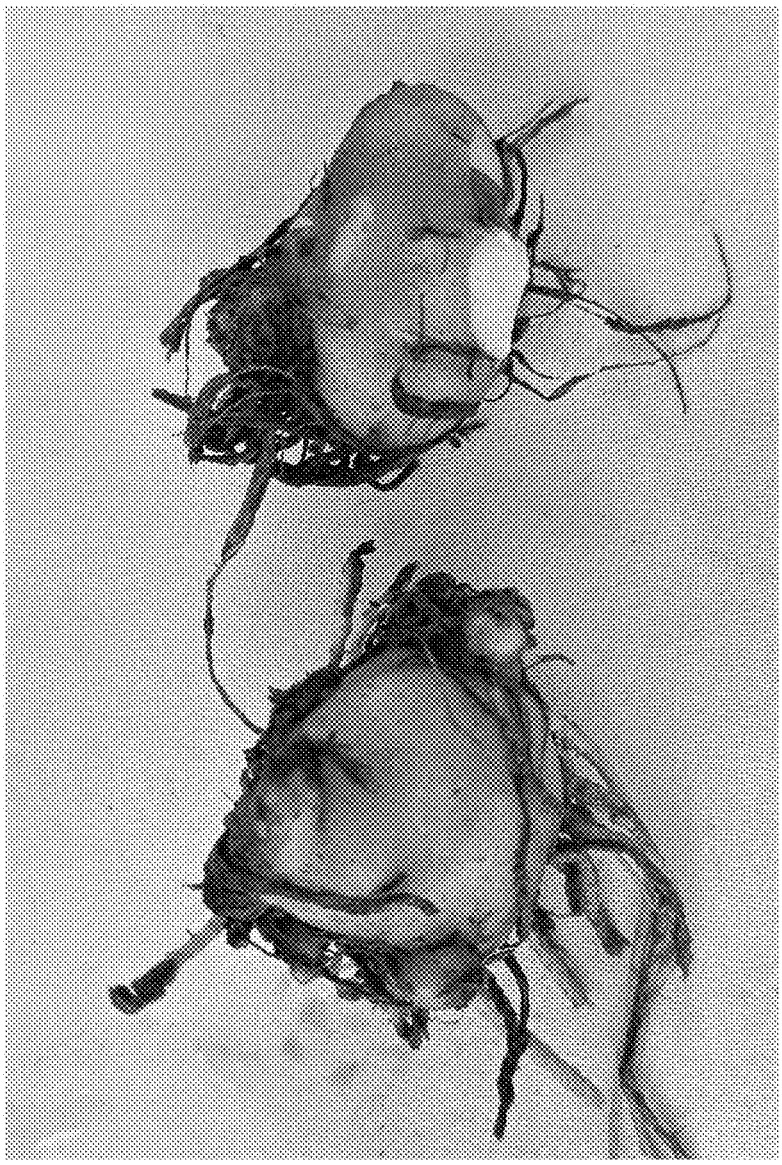

The photograph on the fourth sheet FIG. 6 is a close-up view of typical freshly-harvested tubers with roots of 'FRH OF13-246'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were eight weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'FRH OF13-246'.

Parentage:

*Female, or seed, parent.*—*Caladium* X *hortulanum* 'RUF 1522-3', disclosed in U.S. Plant Pat. No. 33,615.

*Male, or pollen, parent.*—*Caladium* X *hortulanum* 'Frieda Hemple', not patented.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented and branched; individual segments are ovate, elliptic or irregular in shape. Height: About 3.6 cm to 4.2 cm. Diameter: About 4.2 cm to 5.9 cm. Segment height: About 1.7 cm to 3 cm. Segment diameter: About 9 mm to 19 mm. Axillary bud shape: Roughly triangular to elliptic. Axillary bud height: About 3 mm. Axillary bud width: About 3.5 mm to 4 mm. Texture: Thick, starchy; somewhat brittle. Color: Periderm, freshly-harvested: Close to 199A to 199B. Periderm, dried: Close to 200A. Epidermis: Close to 155C tinged with close to 160D. Cortical tissue: Close to NN155A. Axillary buds: Close to 36A to 36B. Root description: Relatively thick, fleshy contractile roots with few lateral branches; color, close to NN155C to NN155D; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 15-cm to 25-cm and suitable as a landscape plant in full sun and shaded areas.

*Plant and growth habit*.—Upright plant habit; tall in height; dense, leafy and bushy appearance; moderately vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 33 cm to 46 cm.

*Plant height, from soil level to top of foliar plane, shade house-grown potted plants, tubers not de-eyed*.—About 51 cm to 66 cm.

*Plant diameter, shade house-grown potted plants, tubers de-eyed*.—About 38 cm to 54 cm.

*Plant diameter, shade house-grown potted plants, tubers not de-eyed*.—About 42 cm to 60 cm.

*Number of shoots per plant, shade house-grown potted plants, tubers de-eyed*.—About five to eleven develop per #1 tuber.

*Number of shoots per plant, shade house-grown potted plants, tubers not de-eyed*.—About two to three develop per #1 tuber.

*Cataphylls, shade house-grown potted plants*.—Length: About 7.5 cm to 8.5 cm. Width: About 1 cm to 1.2 cm. Shape: Lanceolate to wedge-shaped. Apex: Acute to emarginate. Base: Sheathing the stem. Texture, outer and inner surfaces: Smooth, glabrous. Color, outer surface: Close to 199A; color becoming closer to 200A and 200B with subsequent development. Color, inner surface: Close to 200A to 200B.

Leaf description:

*Arrangement and type*.—Alternate; simple; fancy-type.

*Length, shade house-grown potted plants, tubers de-eyed*.—About 17.5 cm to 24 cm.

*Length, shade house-grown potted plants, tubers not de-eyed*.—About 21 cm to 30 cm.

*Width, shade house-grown potted plants, tubers de-eyed*.—When flattened, about 10.5 cm to 14 cm.

*Width, shade house-grown potted plants, tubers not de-eyed*.—When flattened, about 15 cm to 22 cm.

*Shape*.—Ovate with cordate tendencies.

*Apex*.—Acuminate to acute.

*Base*.—Sagittate to peltate, cordate.

*Margin*.—Entire; wavy with broad undulations.

*Texture and luster, upper surface*.—Smooth, glabrous; dull sheen.

*Texture and luster, lower surface*.—Smooth, glabrous; glaucous; dull sheen.

*Venation pattern*.—Pinnate and palmate.

*Color, shade house-grown potted plants*.—When developing and fully expanded leaves, upper surface: Centers: Close to 53A and between 53A and 53B. Marginal areas: Darker than NN137A variably flushed with close to 187A; edges, close to 187A. Basal notch: Close to N186C. Midvein and primary venation: Darker than 53A. Secondary venation: Close to 53A. When developing and fully expanded leaves, lower surface: Centers: Close to 187B, close to 187C tinged with close to 53A and/or close to 191A tinged with close to 189A with flecks, close to 27D. Marginal areas: Close to 191A tinged with close to 189A; edges, close to 187A. Basal notch: Close to 187A. Venation: Close to 185A; surrounding veins, close to 187C tinged with close to 53A.

*Petioles*.—Aspect: Initially upright and straight and leaning outwardly with development; flexible. Length, shade house-grown potted plants, tubers de-eyed: About 30.5 cm to 38 cm. Length, shade house-grown potted plants, tubers not de-eyed: About 32.5 cm to 56 cm. Diameter, distally, shade house-grown potted plants, tubers de-eyed: About 4 mm to 4.5 mm. Diameter, proximally, shade house-grown potted plants, tubers de-eyed: About 5 mm to 8 mm. Diameter, distally, shade house-grown potted plants, tubers not de-eyed: About 4.5 mm to 5.5 mm. Diameter, proximally, shade house-grown potted plants, tubers not de-eyed: About 10 mm to 11 mm. Texture: Smooth, glabrous; slightly glaucous. Color, shade house-grown potted plants: Close to 202A; occasionally, close to 56D densely streaked, striped and tessellated with closer to N200A and 202A; just below the leaf junction, close to 185A and 202A. Wing length, shade house-grown potted plants: About 7.2 cm to 13 cm. Wing diameter, shade house-grown potted plants: About 5 mm to 8 mm. Texture and luster, inner and outer surfaces: Smooth, glabrous; glossy. Wing color, shade house-grown potted plants: Outer surface: Close to N155B and NN155C streaked, stippled and mottled with close to N200A. Inner surface: Close to NN155C with streaks and venation, close to N186B; colors and patterns from the outer surface are visible on the inner surface.

Inflorescence description: To date, inflorescence development has not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'FRH OF13-246' as illustrated and described herein.

* * * * *